(12) United States Patent
Baumgartner et al.

(10) Patent No.: US 9,199,237 B2
(45) Date of Patent: Dec. 1, 2015

(54) AUTOMATED WELL PLATE

(71) Applicants: Michael Baumgartner, Winter Park, FL (US); Michael Nawrocki, Houston, TX (US)

(72) Inventors: Michael Baumgartner, Winter Park, FL (US); Michael Nawrocki, Houston, TX (US)

( * ) Notice: Subject to any disclaimer, the term of this patent is extended or adjusted under 35 U.S.C. 154(b) by 134 days.

(21) Appl. No.: 14/018,385

(22) Filed: Sep. 4, 2013

(65) Prior Publication Data

US 2014/0065661 A1 Mar. 6, 2014

Related U.S. Application Data

(60) Provisional application No. 61/696,547, filed on Sep. 4, 2012.

(51) Int. Cl.
*A61B 10/00* (2006.01)
*B01L 3/00* (2006.01)
*G01N 35/04* (2006.01)
*B01L 3/02* (2006.01)

(52) U.S. Cl.
CPC ........... *B01L 3/5085* (2013.01); *B01L 3/50255* (2013.01); *G01N 35/04* (2013.01); *B01L 3/0293* (2013.01); *B01L 2300/0829* (2013.01); *B01L 2400/0457* (2013.01); *B01L 2400/0487* (2013.01); *G01N 2035/042* (2013.01)

(58) Field of Classification Search
CPC ........................ B01L 3/50255; B01L 2200/025
See application file for complete search history.

(56) References Cited

U.S. PATENT DOCUMENTS

| | | | |
|---|---|---|---|
| 4,118,280 A | 10/1978 | Charles et al. | |
| 4,673,657 A | 6/1987 | Christian | |
| 4,890,930 A | 1/1990 | Nohso | |
| 5,343,909 A | 9/1994 | Goodman | |
| 5,358,871 A | 10/1994 | Stevens et al. | |
| 5,415,840 A | 5/1995 | Sano et al. | |
| 6,086,824 A | 7/2000 | Fanning et al. | |
| 6,159,368 A * | 12/2000 | Moring et al. | 210/321.75 |
| 7,721,947 B2 | 5/2010 | Bjerke et al. | |

FOREIGN PATENT DOCUMENTS

EP 0590485 B1 4/1994
WO WO2007149311 A2 12/2007

* cited by examiner

*Primary Examiner* — Jyoti Nagpaul
(74) *Attorney, Agent, or Firm* — Timothy H. Van Dyke; Beusse, Wolter, Sanks & Maire, PLLC

(57) ABSTRACT

Disclosed in an embodiment herein is a well plate system including a well plate device, including three plates disposed above one another. The two top plates include wells disposed therein which are in fluid communication with one another, and which when the device is in a resting position, the second plate rests on top of the third plate to create a fluid sealed well. The third plate includes fluid drainage openings, such that when the system is in an activated position, the plates are moved such that the fluid within the wells exits through these openings. The system can be fully automated, and can include one or more motors to control movement of the plates. The system can also operate manually with a hinge connected to the plates.

26 Claims, 7 Drawing Sheets

AUTOMATED WELL PLATE

CROSS REFERENCE TO RELATED APPLICATIONS

This application claims priority to Provisional Application No. 61/696,547 filed on Sep. 4, 2012.

BACKGROUND

The use of multi well plates in tissue processing is known. Well plates are known to provide a means to expose a tissue sample or other sample to various reagents. Oftentimes in traditional well plate processes pipettes are used to transfer the reagents into the wells and/or to remove the reagents from the wells. The reagents may also be removed by turning the well plate upside down such that any excess fluid can escape from the plate. This process can be time consuming and inefficient. Furthermore, using a pipette to transfer contents into and out of a tissue or other sample-containing well often results in tissue samples, which are often thin tissue samples, being frequently torn or punctured by pipettes.

DETAILED DESCRIPTION

Figures 1A, 1B:
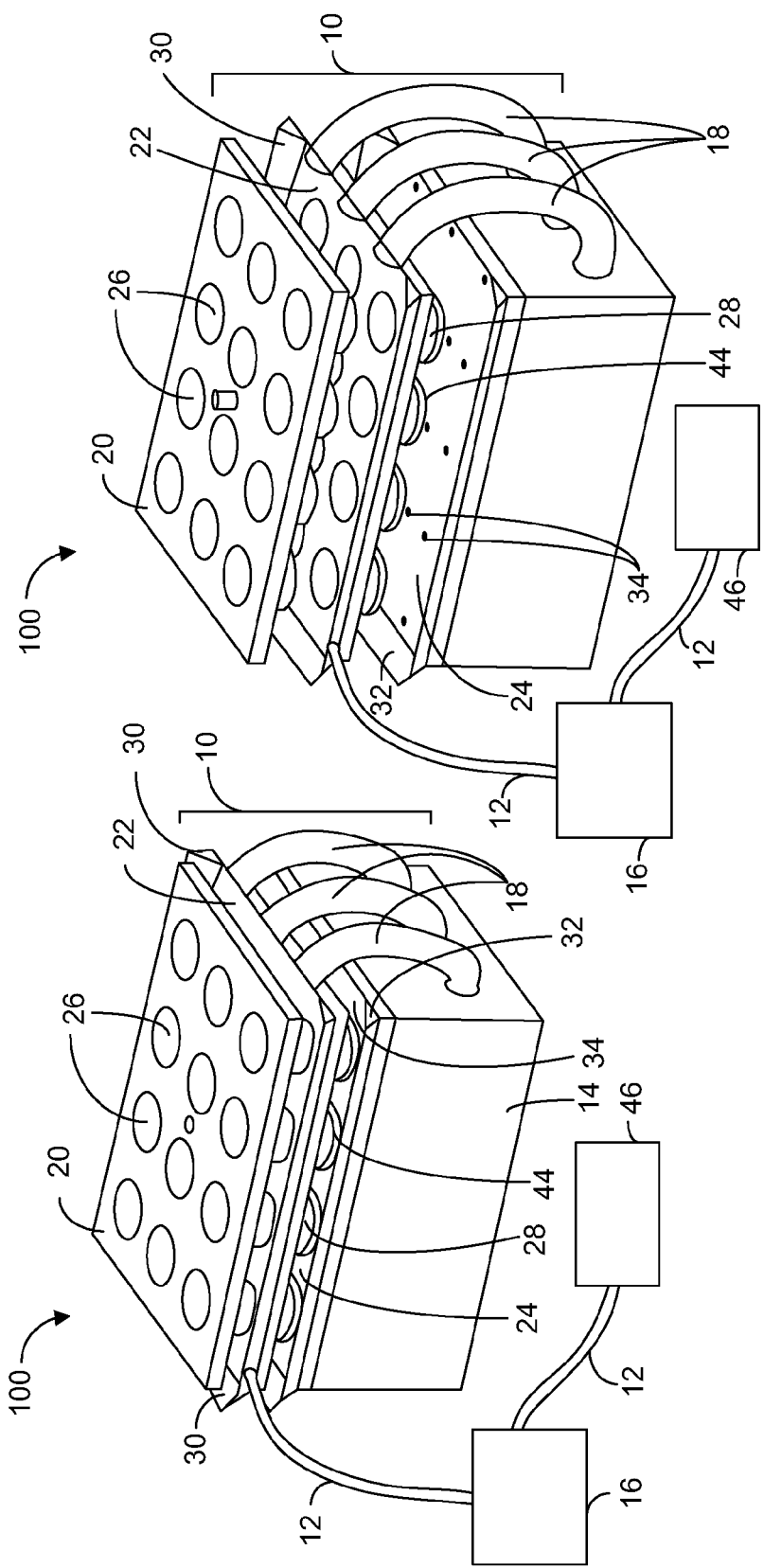
FIG. 1A provides a perspective view of an embodiment of a well plate system comprising a well plate device, wherein the device is in a resting position.
FIG. 1B provides a perspective view of an embodiment of the well plate system shown in FIG. 1A, including a well plate device, wherein the device is in an activated position.

A more particular description of the invention briefly described above will be rendered by reference to specific embodiments thereof that are illustrated in the appended drawings. Understanding that these drawings depict only typical embodiments of the invention and are not therefore to be considered to be limiting of its scope, the invention will be described and explained.

It has been identified herein that pipettes used to transfer reagents into and out of wells in well plates require a significant amount of time manually transferring reagents from one well to another or into and/or out of each well. Moreover, using a pipette to remove reagent from a well plate could damage the tissue sample located therein. Consequently, it has been discovered herein a novel automated well plate system including a multi layer well plate structure, wherein any fluid in the well plate can be easily drained from the well without the use of a pipette. As a result, less time can be spent manually filling and emptying wells and the process is more efficiently conducted. The inventors have discovered, as described in more detail below, a well plate system which features, in some embodiments, automated self-filling and automated self-draining of the wells. The system includes a well plate device including multiple plates, in some embodiments.

In one embodiment, a well plate system is provided herein. The well plate system includes a well plate device which includes a first plate, including one or more wells. Each of said one or more wells including a well wall and a fluid permeable bottom surface. A second plate is also provided, the second plate being disposed beneath the first plate, the second plate comprising a top side, a bottom side, and an outer edge around the perimeter of the second plate. The second plate includes a fluid containment border around at least a portion of the outer edge and one or more wells, wherein each of the one or more wells includes a well wall. A third plate may also be provided, and may be disposed beneath the second plate. The third plate includes a top side, a bottom side, an outer edge around the perimeter of the plate, and a fluid containment border around at least a portion of the outer edge such that when the first second and third plates are associated together in a resting position at least one well of the second plate is aligned with at least one well of the first plate thereby providing a fluid communication there between. The second plate may abut against the third plate top side to form at least one fluid sealed well.

The third plate may include at least one drainage opening extending there through such that when the system is in a resting position, the at least one drainage opening is blocked, and when the second and third plates are dissociated to form an activated position, the at least one drainage opening is unblocked.

In a further embodiment, the system is provided wherein the first, second and third plates are mechanically and/or electrically connected to one another. The mechanical connection may include a hinging arm, in one embodiment, which can be manually manipulated by a user of the system. Other mechanical connections known to those of skill in the art are contemplated herein.

In yet a further embodiment, a first motor, a processor, and a controller are in electrical communication with the first and second plates, and/or the third plate to provide movement of the plates. In some embodiments, this movement of the plates is automated. In yet a further embodiment, one of the first and second plates and the third plate is vertically adjustable relative to the other of the first and second plates and the third plate. In a particular embodiment, the third plate is stationary and the first and second plates are vertically movable relative to the third plate.

In still a further embodiment, one of either the first and second plates or the third plate is horizontally adjusted relative to the other of the first and second plates and the third plate. In another embodiment, both of the first and second plates and the third plate are moved vertically in opposite directions from one another to create a gap between the second plate and the third plate. In yet another embodiment, both of the first and second plates and the third plate are moved horizontally in opposing directions, for example, such that at least one of the wells of the first and second plates align with at least one of the fluid drainage openings of the third plate to form a fluid connection there between. In other embodiments, a drainage container is disposed below the third plate. In some instances the drainage container is provided to contain the fluid which exits the third plate through the fluid drainage opening(s).

In some embodiments, a sealing material surrounds the portion of the cylindrical wall of the one or more wells of the second plate adjacent to the third plate, such that when the one or more wells of the second plate contact the third plate, a seal is created there between.

In an embodiment, at least a portion of the bottom surface of the one or more wells comprises a fluid permeable material, a mesh material, or a solid surface with one or more openings there through or any surface known to those of skill in the art to provide a fluid communication between the first and second plates.

In a further embodiment, a second motor is in electrical communication with the first and/or second plates to provide horizontal movement of the plate(s). In one embodiment, the horizontal movement can provide a mechanical agitation of the plate(s). In a particular embodiment, the second motor is a rotary motor, provided to shake the plate(s). The first and second motors and supporting struts will be used to provide movement of the plates as discussed herein. In some embodiments, one motor may be configured to control both the vertical and the horizontal movement of the plates described herein. Alternatively, additional motors may be included in the system to control movement of the plates herein.

In yet a further embodiment, a pump and a delivery conduit are connected between the first or second plate and a delivery container, wherein the delivery container is configured to house a fluid, for example, to be pumped into the one or more wells of the first or second plate via the pump and the delivery conduit. The fluid may include a reagent or other fluid to be introduced to a well or tissue sample. In other embodiments, multiple delivery containers may be associated with the first and/or second plates of the system such that the multiple delivery containers are configured to house fluids for introduction to the system. The delivery containers may each include different fluids or reagents or the same fluid or reagent.

The pump may be electrically connected to a power source, in one embodiment. In another embodiment, a draining conduit may be associated with the first and/or second plate(s) such that excess fluid from the first and/or second plate(s) may be collected by the draining conduit. The draining conduit may be connected between the first and/or second plate and the drainage container, in one embodiment. In another embodiment, as described herein, a drainage container may not be provided. In this particular embodiment, the system may be placed over a sink such that the fluid drains directly from the device into the sink. Alternatively, in other embodiments, the draining conduit may drain fluid into a sink or other vestibule or chamber located on or near the system.

In another embodiment, a method of tissue processing using the system above is provided, the method includes inserting a sample into the one or more wells of the first plate, wherein the first plate is vertically disposed above the second plate. The method further includes initiating a fluid delivery system including a pump and a fluid conduit to pump a first fluid into one or more wells of the second plate, wherein after the one or more wells of the second plate are filled, any excess of the first fluid that remains is removed from the second plate by at least one drain conduit. The method further includes activating a first motor associated with the system to vertically lower the first plate onto the second plate, wherein the one or more wells of the first and second plates are vertically aligned, such that the first fluid from the one or more wells of the second plate passes into the one or more wells of the first plate to contact the sample. The method further includes activating the first motor to vertically raise the first plate, such that the first fluid drains from the one or more wells of the first plate into the one or more wells of the second plate and activating the first motor to vertically raise the second plate such that the seal between the second and the third plate is broken such that the first fluid drains from the second plate onto the third plate and through the at least one drainage opening in the third plate.

The vertical movement of the second plate may occur in place of the vertical movement of the first plate, in an embodiment, allowing the first fluid to drain through the wells of both the first plate and the second plate onto the third plate and through the at least one drainage opening in the third plate. Vertical movement of the second plate in an upward direction, away from the third plate, may work to move both of the first and second plates vertically upward allowing the fluid to drain from both plates. Alternatively, vertical movement of the third plate away from the second plate (i.e., downward vertical movement) would result in drainage of the fluid from the first and second plates as well. Any of these movements would have the same or a similar result and thus are contemplated as part of the invention herein.

In a further embodiment, the method includes wherein the first motor is activated to vertically lower the second plate onto the third plate creating a seal between the one or more wells of the second plate and the third plate. The fluid delivery system would thereby be activated to initiate the pump to pump a second fluid into the second plate via the conduit wherein the second fluid is pumped into the one or more wells of the second plate, in one embodiment. The introduction of a second fluid to the second plate is not required, however, it allows for the introduction of multiple different fluids to the sample. In this manner, the process may be repeated over a number of times with multiple fluids. Additional pumps and fluids may be provided as part of the system and the process may be repeated until all the fluids have been associated with the sample.

In still a further embodiment, the method includes activating a second motor to provide horizontal movement of the plate to provide a mechanical agitation of the plate. The method may be provided, alternatively or in addition to the mechanical agitation of the plate, wherein the agitation of the first and second plates is not controlled by a motor.

In another embodiment, a well plate system is provided, the well plate system includes a well plate device, a first plate comprising a top surface, a bottom surface and an outer edge surface, the first plate having openings extending from the top surface to the bottom surface, wherein each of the openings are configured to receive a well comprising a wall and a bottom surface. The embodiment includes a second plate having a top surface, a bottom surface and an outer edge surface around the perimeter of the plate. The second plate includes a fluid containment border around the outer edge surface, the second plate having openings extending from the top surface to the bottom surface, the openings configured to receive a well, and the well includes a wall. The well plate system further includes a third plate comprising a top surface, a bottom surface, and an outer edge surface around the perimeter of the plate. The third plate includes drainage openings extending from the top surface to the bottom surface of the third plate, and a border surrounding at least a portion of the outer edge. The system may further include a first motor electrically connected to at least one of the first, second and third plates, wherein the first motor may provide movement of at least one of the first, second and third plates relative to at least another of the first, second and third plates.

The system described herein may include any number of plates and any number of wells and openings there through. While the system is described herein and shown in the drawings as including three plates, it is not limited to three plates and may include between 2-10 plates or between 3-6 plates in different embodiments.

Turning to the Figures, in the embodiment of the well plate system 100 of FIGS. 1A and 1B, FIG. 1A illustrates the well plate system 100 in a resting position, and FIG. 1B illustrates the well plate system 100 in an activated position. The well plate device 10 of the well plate system 100 includes three plates, a first plate 20 housing multiple first plate wells 26 into which a sample (sample not shown in FIGS) can be placed, a second plate 22 housing multiple second plate wells 28 and a second plate fluid containment border 30 surrounding at least a portion of an outer edge of the second plate 22. The second plate fluid containment border 30 serves to contain the fluid on the second plate 22 and prevents the fluid from dripping over the side of the second plate 22. The second plate wells 28 are provided of a size and shape such that the first plate wells 26 fit within the second plate wells 28, in one embodiment, when the system 100 is in a resting position as in FIG. 1A. The second plate wells 28 may include a sealing member 44 around a portion thereof. A third plate 24 is provided, disposed below the second plate 22, the third plate including drainage openings 34 which allow fluids on the third plate to be drained into a drainage container 14 provided there below, and the third plate 24 including a third plate fluid containment border 32. The third plate fluid containment border 32 surrounds at least a portion of the outer edge of the third plate 24 to prevent fluid from escaping over the edge of the third plate 24. In some embodiments, the system 100 may not include a drainage container 14, but may instead be placed over a sink, for example, during use such that any excess fluid may drain directly from the device 10 into the sink.

The device 10 may further include at least one draining conduit 18 which connects between the second plate 22 and the drainage container 14 to collect excess fluid from the second plate 22 and remove the fluid from the second plate 22 by way of the draining conduit 18. More than one drainage container 14 may be provided as part of the system 100, while only one drainage container 14 is shown in the Figures herein. Draining conduits 18 may alternatively connect to the second plate 22 at one of the ends of each of or at least one of the draining conduits 18 wherein the other ends of each of (or one of) the draining conduits 18 are free such that the draining conduit(s) 18 can drain fluid from the second plate 28 into any receptacle available if no drainage container 14 is provided. If a drainage container 14 is provided, it may be emptied periodically or once testing of the sample is complete. In some embodiments, no draining conduits 18 are provided.

Figure 4:
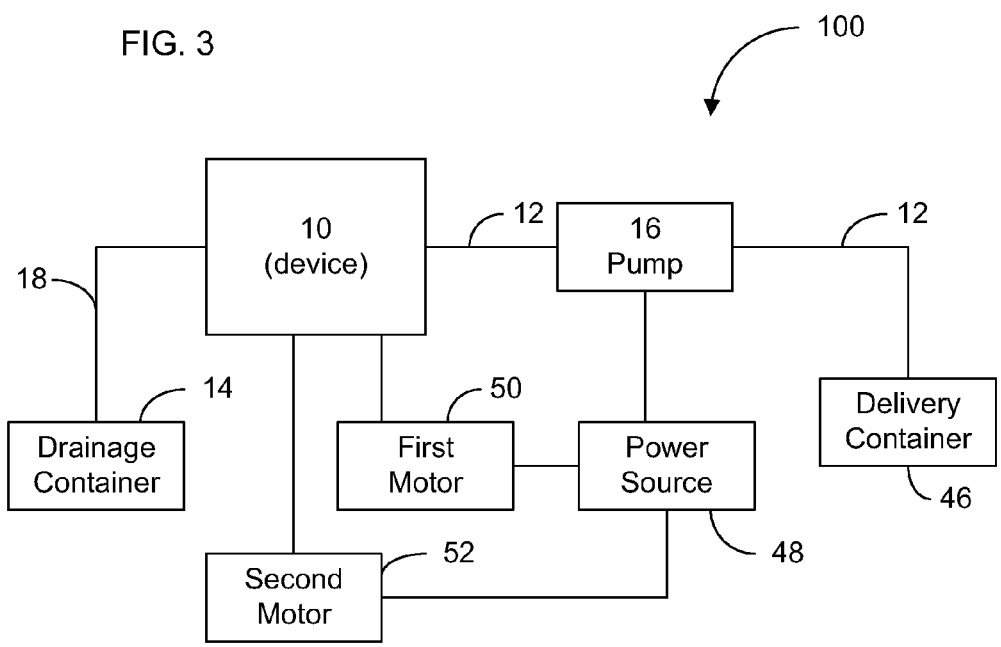
FIG. 4 provides a schematic depicting the connections between the components of an embodiment of the well plate system.

A delivery conduit 12 may be connected between a delivery container 46 and the second plate 22, in one embodiment, as shown in FIGS. 1A-1B (and FIG. 4 described in more detail below), wherein a fluid communication is provided there between. The delivery conduit 12 serves to provide fluid from the delivery container 46 through a pump 16 to the second plate wells 28. The pump 16 may be electrically connected to a power source 48 (as shown in FIG. 4), which may be in the form of a battery, an outlet, or any other power source as known in the art, such that sufficient power is provided to activate and conduct the various functions and operate the various components of the system 100. Alternatively, the pump 16 may be manually operated.

The system 100 may further include a first motor 50 (as shown in FIG. 4), wherein the first motor 50 is in electrical communication with the device 10 and the power source 48 such that automated movement of the first plate 20, second plate 22, and/or third plate 24 is possible. In some embodiments, as already mentioned above, and as will be discussed below with regard to FIG. 5, the system 100 may not require a motor. However, in another embodiment, a second motor 52 may be provided (also shown in FIG. 4), wherein it is connected to the power source 48 and the device 10 to provide movement of the first and or second plate 20, 22 in a horizontal plane to provide mechanical agitation of a sample when placed within one of the wells, for example. Additional motors (more than two) may also be used in alternative embodiments, not shown in the Figures herein.

Figure 2A:
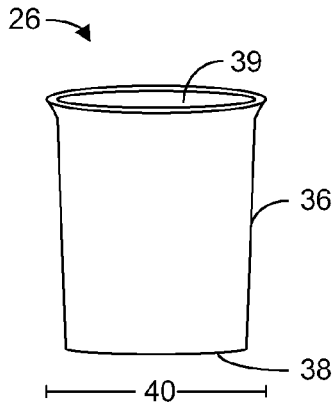
FIG. 2A provides a side view of an embodiment of a first plate well.
Figure 2B:
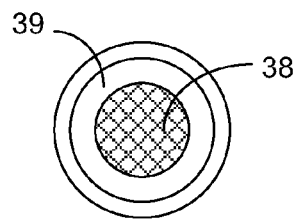
FIG. 2B provides a top end view of an embodiment of a first plate well with a mesh base.
Figure 2C:
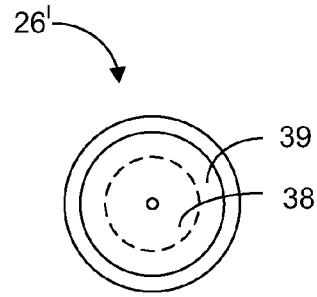
FIG. 2C provides a top end view of an embodiment of a first plate well with a solid base having an opening.

As shown in FIGS. 2A-C the first plate wells 26 are illustrated as being shaped with a cylindrical wall 36 or body in a non-limiting embodiment, and a bottom surface 38 with an open top 39, wherein the wells are of a first diameter 40 (see FIG. 2A). The wells described herein may include other shapes, and are not limited to being cylindrical in shape. For example, the walls of the wells described herein may be square in shape or diamond shaped in other non-limiting embodiments. In certain embodiments the diameter 40 of the first plate wells 26 may vary from the bottom surface 38 to the top 39 of the first plate well 26. In one embodiment, the first diameter 40 may increase from the bottom surface 38 of the well to the top 39, in another embodiment; the first diameter 40 may decrease from the bottom surface 38 to the top 39. Therefore, the numerical value of the first diameter 40 may be a range of values. The bottom surface 38 can be formed of a fluid permeable material embodied as a mesh material or a semi permeable material, in non limiting examples, (as represented in FIG. 2B). Fluid permeable material as used herein includes material capable of being permeated by liquids or gases, including penetrable, porous, pervious materials such as, for example, mesh or any other materials which are known in the art to achieve the same purpose as provided and described in the FIGS and the description herein. The first plate wells 26 which comprise a bottom surface 38 formed at least partially of a mesh material are beneficial for retaining and testing of tissue samples, in a non-limiting example. First plate wells 26 having a semi-permeable membrane as all or part of their bottom surface 38, may be particularly beneficial for use in cell-based sample testing. The bottom surface 38 of the wells 26 can alternatively be formed as a solid base with one or more openings located in the bottom surface 38 to allow for draining of the first plate well 26 (one opening in the bottom surface 38 is shown in FIG. 2C). The well embodiment shown in FIG. 2C may be particularly useful, as a non-limiting example, for use with antibody samples.

Figure 3:
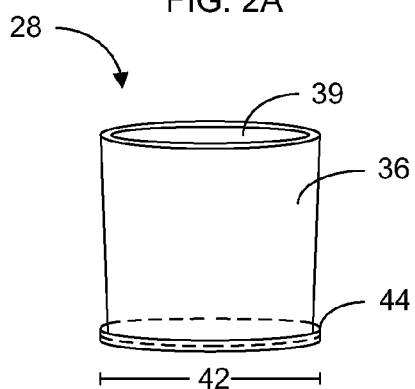
FIG. 3 provides a side view of an embodiment of a second plate well.

The second plate wells 28 can be of a second diameter 42 which may be larger than the first diameter 40 of first plate wells 26 as can be seen in FIG. 3. The diameter of the first plate wells 26 may vary from one to another, as can the diameter of second plate wells 28 (as well as the diameter of the raised members 56 shown in FIG. 8 as described below). An additional difference between the first plate wells 26 and the second plate wells 28 is that while the second plate wells 28 comprise a cylindrical wall 36 or body, in one embodiment, and an opening at the top 39, similar to the first plate wells 26, the second plate wells 28 do not include a bottom surface 38. The second plate wells 28 are configured, in some embodiments as aforementioned, to include a sealing member 44 around the lower surface or toward the lower portion of the second plate well 28. The sealing member 44 may include any type of sealing device known in the art, including but not limited to a rubber or similar material in the shape of an O-ring which surrounds the base of the second plate wells 28, in a non-limiting example. The sealing member 44 is provided such that when the second plate wells 28 rest on a surface of a third plate 24 which is disposed below the second plate 22, a seal is formed between the two plates wherein any fluid that is placed within the first or second plate wells 26, 28 is contained within the second plate wells 28. Once the seal achieved at least in part by the sealing member 44, in some embodiments, between the second plate 22 and third plate 24 is broken (i.e. once the second plate 22 or third plate 24 is moved to loosen or remove the sealed connection between the second plate wells 28 and the third plate 24), any fluid contained within the second plate wells 28 drains through the one or more drainage openings 34 in the third plate 24.

The drainage openings 34 may drain the fluid into a drainage container 14 associated with the device 10. However, no drainage container 14 is required, as the device 10 can be placed over and/or drained into a sink or other receptacle, for example.

Figure 5:
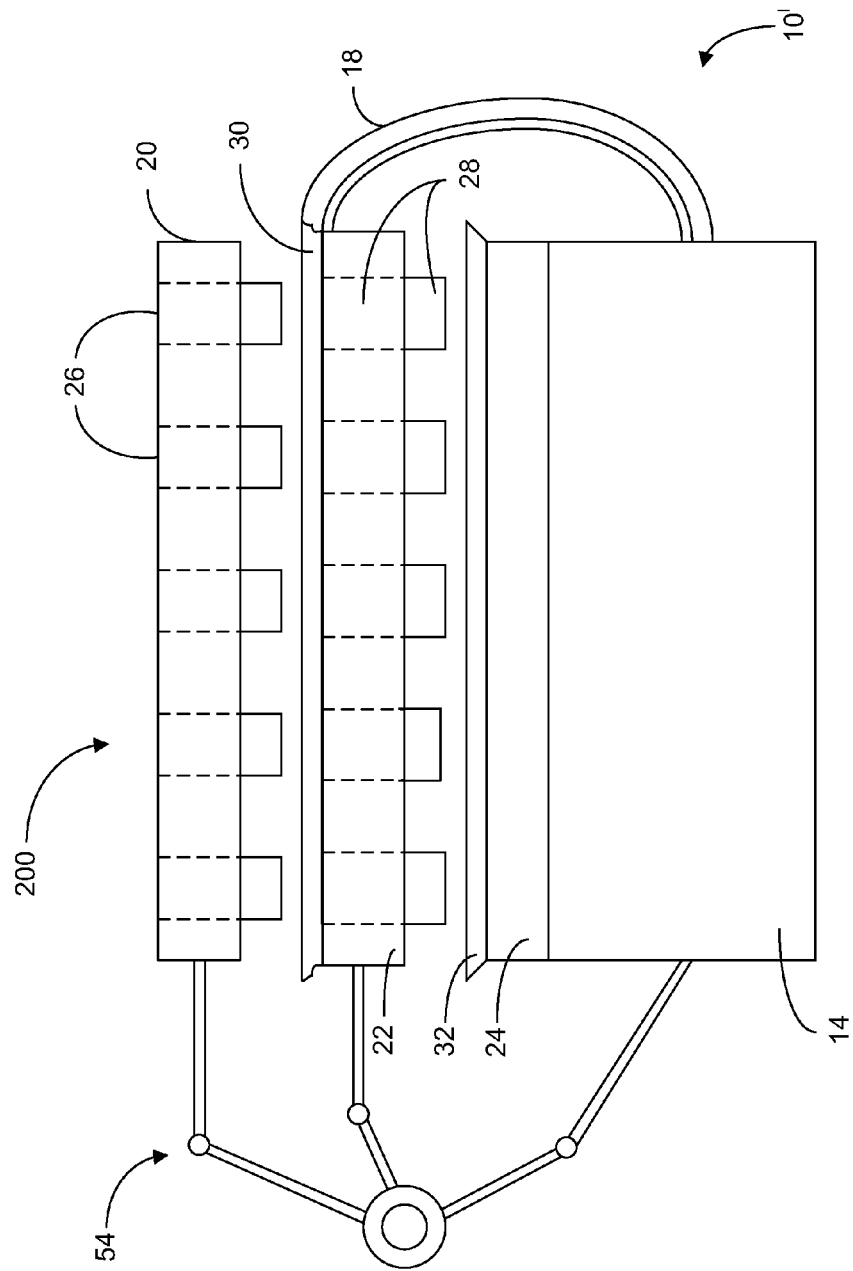
FIG. 5 provides a front side view of an embodiment of the well plate system wherein a hinging arm is provided for movement of the plates relative to one another.

FIG. 4 provides a schematic of the system 100, wherein electrical communications and fluid communications between the components of the system 100 are illustrated. FIG. 4 illustrates the electrical connections of the first motor 50 and the second motor 52 between the device 10 and the power source 48. FIG. 4 further demonstrates the pump 16 being electrically connected to and powered by the power source 48, wherein the pump 16 is disposed between and in fluid communication with the device 10 and the delivery container 46. The delivery conduit 12 provides fluid communication between the delivery container 46 and the pump 16, and the pump 16 and the device 10. The power source 48 can be embodied as is known in the art including, for example, an external power source, a battery or series of batteries used to power the system 100, or by any other means known in the art. A drainage container 14 is shown as in fluid connection with the device 10 via a draining conduit 18. FIG. 5 provides another embodiment of a well plate system 200. This embodiment includes a hinging arm 54 which is used as a mechanical connection or mechanical device to move the first plate 20, second plate 22, and/or third plates 24 of an embodiment of the well plate device 10' used by a user of the device 10' to manually raise or lower the plates relative to one another. The components of the hinging arm 54 (e.g. the individual arms) may include biasing members, wires, or other types of devices which serve to hold the plates in place once they are moved into a position.

Figure 6:
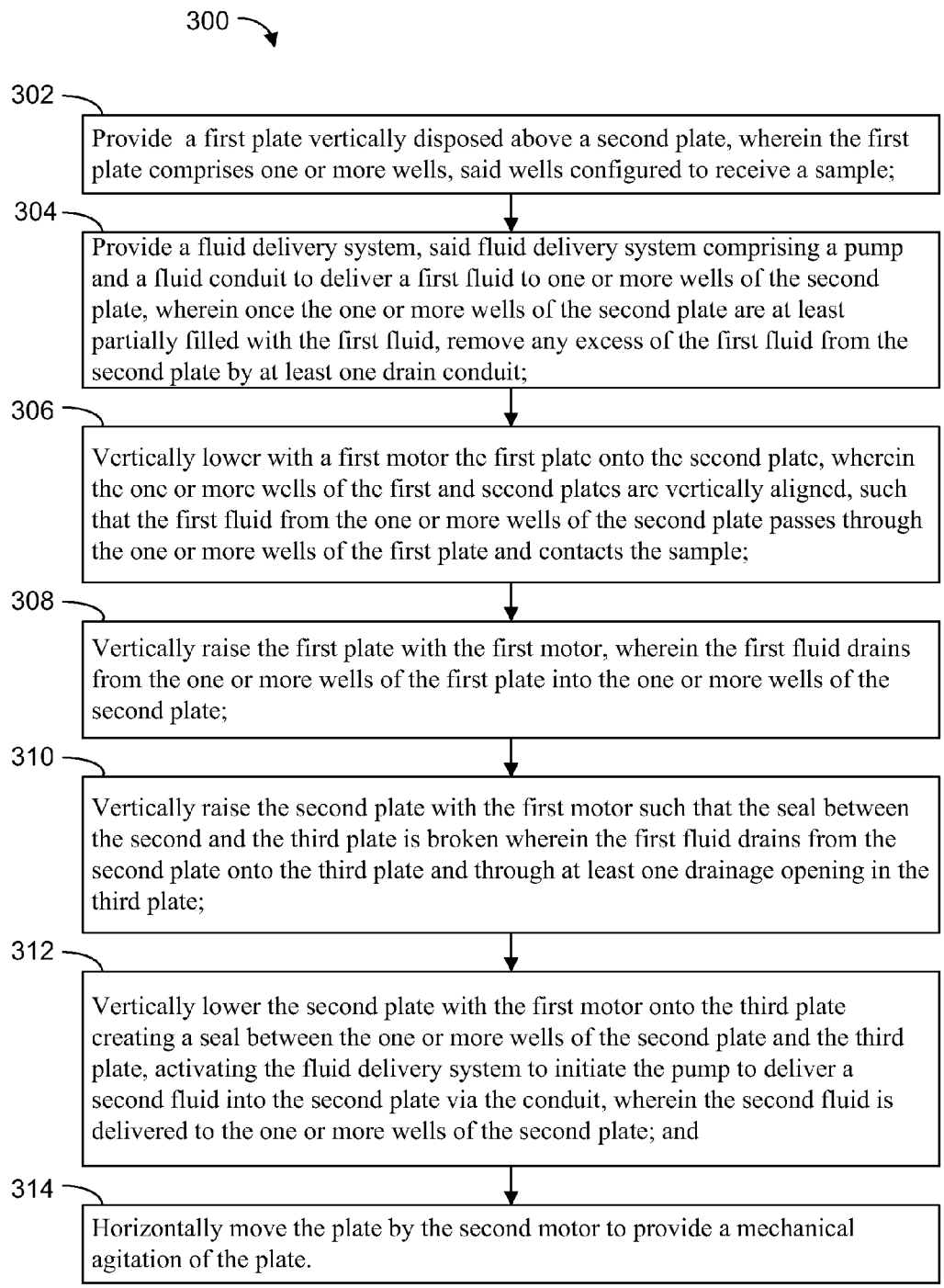
FIG. 6 is a flow chart including steps in one embodiment of a method or process of tissue processing using a well plate system.

FIG. 6 provides a diagram illustrating a method 300 of tissue processing using the well plate system 100. The method 300 includes a step 302 of providing a first plate 20 vertically disposed above a second plate 22, wherein the first plate 20 comprises one or more first plate wells 26, said wells 26 configured to receive a sample; and a step 304 of providing a fluid delivery system, said fluid delivery system comprising a pump and a fluid conduit to deliver a first fluid to one or more wells of the second plate 28, wherein once the one or more wells of the second plate 28 are at least partially filled with the first fluid, remove any excess of the first fluid from the second plate by at least one drain conduit. The method further include step 306 of vertically lowering with a first motor 50 the first plate 20 onto the second plate 22, wherein the one or more wells of the first 26 and second plates 28 are vertically aligned, such that the first fluid from the one or more wells of the second plate 28 passes through the one or more wells of the first plate 26 and contacts the sample, and step 308 of vertically raising the first plate 20 with the first motor 50, wherein the first fluid drains from the one or more wells of the first plate 26 into the one or more wells of the second plate 28, and step 310 of vertically raising the second plate 22 with the first motor 50 such that a seal 44 between the second plate wells 28 and the third plate 24 is broken, wherein the first fluid drains from the second plate 22 onto the third plate 24 and through at least one drainage opening 34 in the third plate 24.

The method 300 further includes the step 312 of vertically lowering the second plate 22 with the first motor 50 onto the third plate 24 creating a seal 44 between the one or more wells of the second plate 28 and the third plate 24, activating the fluid delivery system to initiate the pump 16 to deliver a second fluid into the second plate 22 via the conduit 12, wherein the second fluid is delivered to the one or more wells of the second plate 28, and horizontally moving 314 the first and/or second plate 20, 22 by the second motor 52 to provide a mechanical agitation of the first and/or second plate 20, 22.

Figure 7:
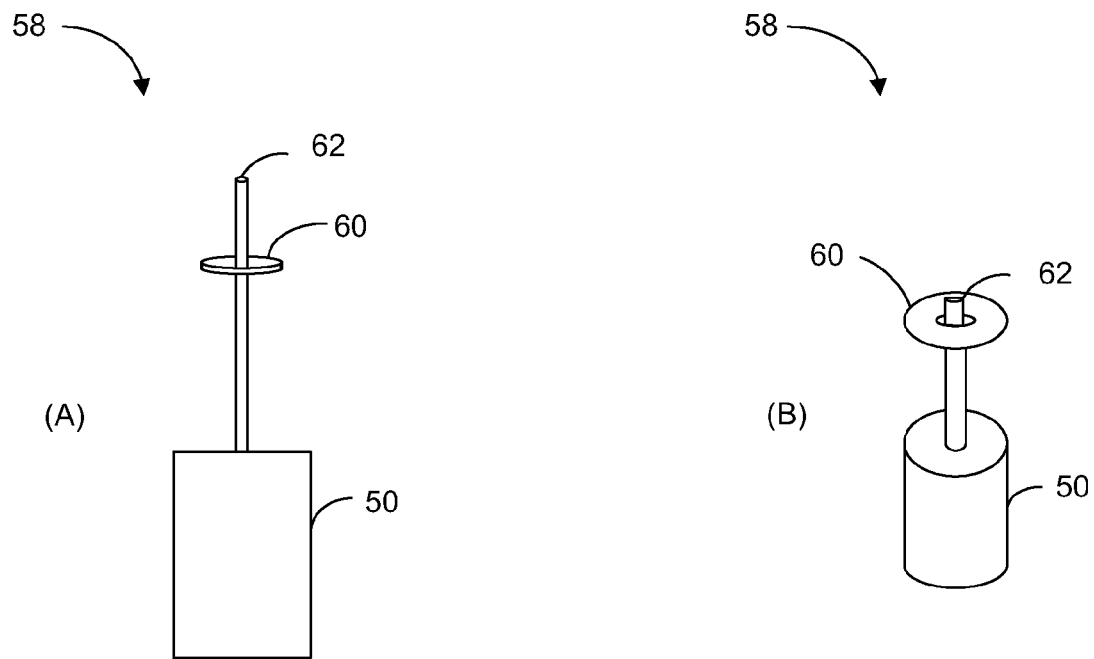
FIG. 7 provides a front view of a "t" bar embodiment of the system.
Figure 7:
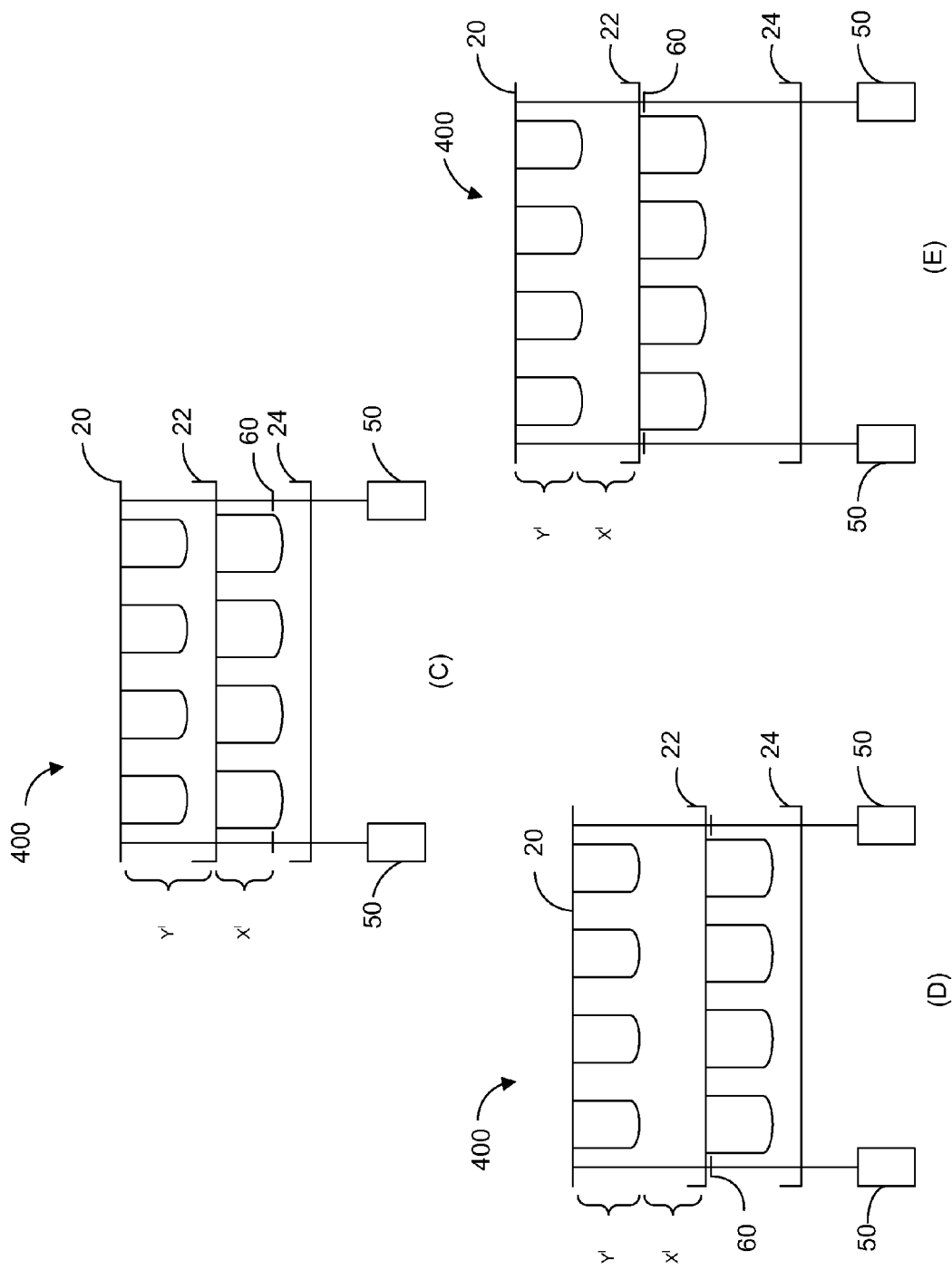

FIG. 7 illustrates an embodiment of the invention 400 providing a "T" bar 58 associated with a first motor 50 on opposing sides of the plates provided to vertically adjust the plates. A second motor 52 may be provided in an alternative embodiment in place of the first motors 50 in FIG. 7, or in place of one of the first motors 50 to provide horizontal agitation. The T bar includes a tip 62 at its upper most point, a first or second motor 50, 52 (first motor 50 shown in FIG. 7) at its lower end and a catch 60 disposed there between as shown in the side view of FIG. 7A and the perspective top and front view of FIG. 7B. The first plate 20 can be attached directly to or near the tip 62 of the T bar 58 as shown in FIG. 7C. In a resting position as shown in FIG. 7C, there is a distance x' between the second plate 22 and the catch 60, and a distance y' between the first plate 20 and the second plate 22. This orientation allows the top plate 20 to be raised a distance x' whereby the "T" portion of the T bar moves upwardly in a vertical direction until the catch 60 contacts the second plate 22 (see FIG. 7D) before the second plate 22 is vertically moved. Once the catch 60 contacts the second plate 22, the second and first plates 22, 20 are both raised by the T bar if any additional upward vertical movement of the plates is necessary (see FIG. 7E).

Figure 8:
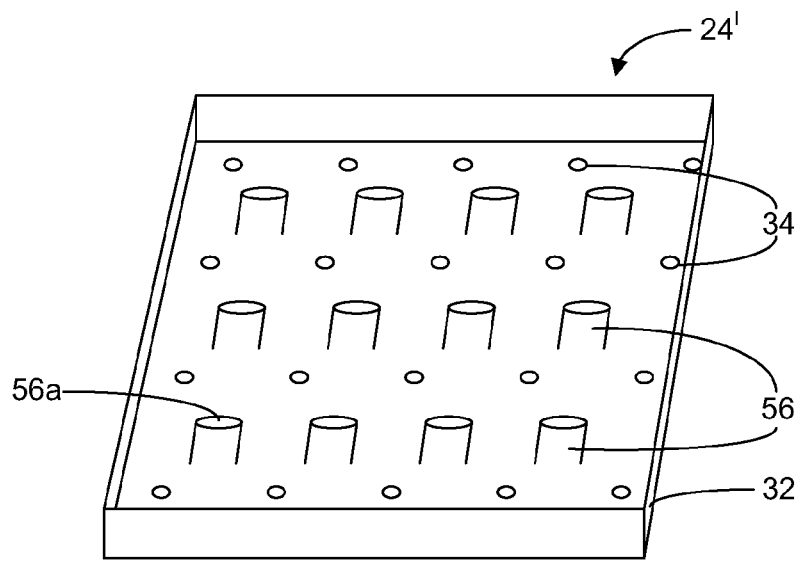
FIG. 8 provides a top perspective view of another embodiment of the third plate according to the invention.

FIG. 8 provides a further embodiment of the third plate 24', wherein raised members 56 are disposed on the top side of the third plate 24' such that at least one raised member 56 aligns with at least one first plate well 26 and one second plate well 28 such that fluid communication can be provided there between. The raised member 56 may be of such a size and shape to receive second plate well 28 from the second plate 22 within the raised member 56, therefore, the raised member 56 may be of a complementary shape to the second plate well 28, however including a greater diameter than the second plate well 28. Alternatively, the raised member may be configured of such a size and shape to fit within the second plate well 28 when the raised member 56 and the second plate well 28 are pressed together. Furthermore, a seal 57 can be created between at least one of the second plate wells 28 and at least one raised member 56 when the second plate 22 is lowered to contact the third plate 24' or the third plate 24' is raised to contact the second plate 22. The seal 57 may be created by nature of the fit between the second plate well 28 and the raised member 56, alternatively a silicone or other material may be placed there between, or an O-ring may be disposed between the second plate well 28 and the raised member 56 to create the seal 57. The embodiment of the third plate 24' provided in FIG. 8 allows a user of the system to adjust the depth or volume of the wells during use of the system 100.

Figure 9:
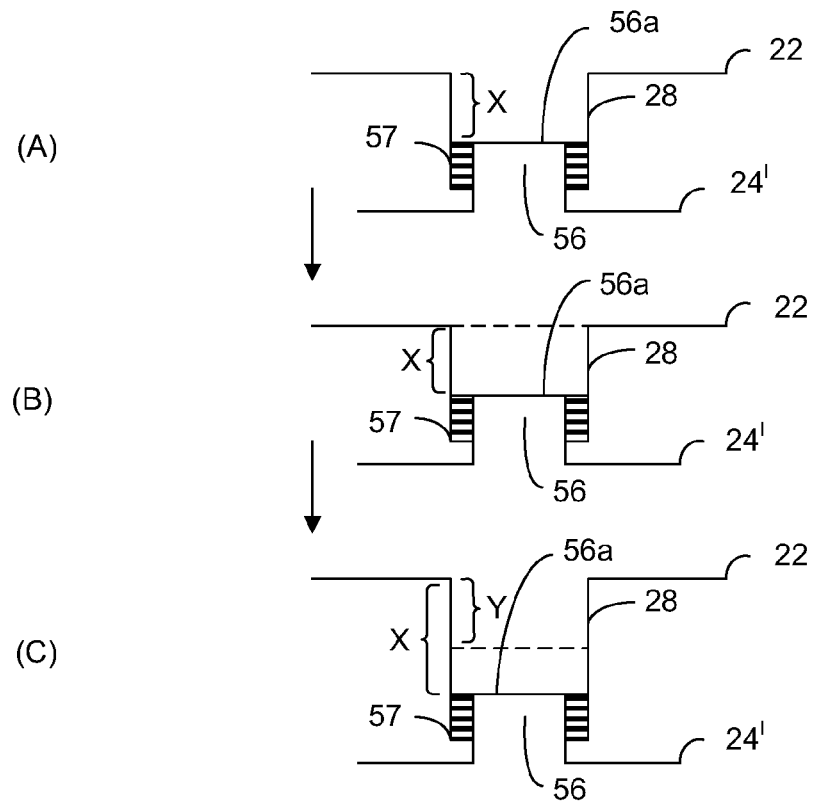
FIGS. 9A-C provides a schematic illustrating the adjustability of the well depth according to an embodiment of the well plate system comprising the third plate embodiment illustrated in FIG. 8.

FIGS. 9A-C provide an example of the adjustability of the well depth according to an embodiment. The third plate 24' is aligned with the second plate 22 such that a second plate well 28 fits over a raised member 56 of the third plate 24', and an "X" distance is created between the top of the second plate 22 and a top portion 56a of the raised member 56 of the third plate 24' (see FIG. 9A). A seal 57 is shown as provided between the raised member 56 and the walls of the second plate well 28. Once fluid is transferred into the second plate 22, the second plate well 28 can be filled with fluid (as shown in FIG. 9B, fluid level is represented by a dotted line) such that the fluid level is even with the level of the second plate 22. Thereafter, (as shown in FIG. 9C), the depth of the fluid level in the second plate well 28 can be adjusted either by moving the second plate 22 vertically upward or the third plate 24' vertically downward such that a distance "Y" between the top of the fluid line and the top of the second plate 22 is increased.

Various advantages are provided by the adjustable well depth embodiment. For example, the depth of the well can be changed during processing of a specimen without requiring an additional motor or plate. The embodiment also minimizes spillage and fluid transfer between the wells. An O-ring, or other device known in the art, as mentioned above, which creates a partial or complete seal 57 can be used between the raised member 56 of the third plate 24' and the well of the second plate 22 so as to prevent or reduce cross contamination and spillage of reagents, for example. Drainage openings 34 are provided on the third plate 24', and are off-set from the raised member(s) 56 of the third plate 24' so that the third plate 24' can be drained.

In the embodiments described herein, a first motor is used to vertically manipulate the first, second and/or third plate(s) of the system, and a second motor is described as horizontally manipulating the first, second and/or third plate(s) of the system. However, any number of motors can be used to either vertically or horizontally manipulate the plate(s). For example, a first motor can be used to vertically adjust the first plate, and a second motor can be used to horizontally move any of the plate (s), a third motor can also be included to vertically adjust the second or the third plate or both or all of the plates, or one motor could perform all vertical and horizontal movements. The system may be included such that any of the plates can be moved independently of the other plates. Furthermore, any number of motors connected to any of the plates is contemplated herein, and would be known to those of skill in the art.

While certain embodiments of the present invention have been shown and described herein, such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. A well plate system, comprising:
   a well plate device, comprising;
      a first plate, comprising one or more wells, each of said one or more wells comprising a well wall and a fluid permeable bottom surface;
      a second plate disposed beneath the first plate, said second plate comprising a top side, a bottom side, and an outer edge around the perimeter of the plate, the plate comprising a fluid containment border around at least a portion of the outer edge, said second plate comprising one or more wells, each of said one or more wells comprising a well wall;
      a third plate disposed beneath the second plate, said third plate comprising a top side, a bottom side, an outer edge around the perimeter of the plate, a fluid containment border around at least a portion of the outer edge, wherein when said first plate, said second plate and said third plate are associated together in a resting position, at least one well of the second plate is aligned with at least one well of the first plate thereby providing a fluid communication there between, and said second plate abuts against the top side of the third plate to form at least one fluid sealed well.

2. The system of claim 1, wherein the third plate comprises at least one drainage opening extending there through, such that when the system is in a resting position, fluid is contained within the fluid sealed well, and when the second and third plates are dissociated to form an activated position, fluid flows through the at least one drainage opening in the third plate.

3. The system of claim 2, wherein a drainage container is disposed below the third plate.

4. The system of claim 1, wherein said first, second and third plates are mechanically and/or electrically connected to one another.

5. The system of claim 4, wherein said mechanical connection includes a hinging arm.

6. The system of claim 1, wherein at least a first motor, a processor, and a controller are in electrical communication with the first plate, the second plate, and/or the third plate to provide automated movement of the plates.

7. The system of claim 6, wherein a second motor is in electrical communication with the first and/or second plates to provide horizontal movement of the first and/or second plate(s) to provide a mechanical agitation of the plate(s).

8. The system of claim 6, wherein a third motor is in electrical communication with the first plate, the second plate, and/or the third plate to provide automated movement of the plate(s) independently of the movement provided by the first motor.

9. The system of claim 1, wherein one of either the first and second plates or the third plate is vertically adjusted relative to the other of the first and second plates and the third plate.

10. The system of claim 1, wherein one of either the first and second plates or the third plate is horizontally adjusted relative to the other of the first and second plates and the third plate.

11. The system of claim 10, wherein the plates are horizontally moved such that the at least one drainage opening in the third plate is aligned with the one or more wells of the first and second plates, forming a fluid connection there between.

12. The system of claim 1, wherein both of the first and second plates and the third plate are moved vertically in opposite directions to create a gap between the second plate and the third plate.

13. The system of claim 1, wherein both of the first and second plates and the third plate are moved horizontally in opposing directions.

14. The system of claim 13, wherein the plates are horizontally moved such that the at least one drainage opening in the third plate is aligned with the one or more wells of the first and second plates, forming a fluid connection there between.

15. The system of claim 1, wherein a sealing material surrounds the portion of the cylindrical wall of the one or more wells of the second plate adjacent to the third plate, such that when the one or more wells of the second plate contact the third plate, a seal is created there between.

16. The system of claim 1, wherein at least a portion of the bottom surface of the one or more wells comprises a fluid permeable material.

17. The system of claim 1, wherein at least a portion of the bottom surface of the one or more wells of the first plate comprises a mesh material.

18. The system of claim 1, wherein at least a portion of the bottom surface of the one or more wells of the first plate comprises a solid surface with at least one opening there through, providing a fluid communication between the first and second plates.

19. The system of claim 1, wherein a pump and a delivery conduit are connected between the first and/or second plate and a delivery container, wherein the delivery container is configured to house a fluid to be pumped into the one or more wells of the first and/or second plate via the pump and the delivery conduit.

20. The system of claim 19, wherein a draining conduit is associated with the first or second plate, such that any excess fluid in or on the first and/or second plate(s) is collected by the draining conduit.

21. The system of claim 20, wherein the draining conduit connects between the first and/or second plate and the drainage container.

22. The system of claim 1, wherein the third plate comprises raised members on its top side, wherein at least one of said raised members are aligned with at least one well of the first and second plates, providing fluid communication there between.

23. A method of tissue processing using a well plate system comprising a well plate device, comprising a first plate, comprising one or more wells, each of said one or more wells comprising a well wall and a fluid permeable bottom surface, a second plate disposed beneath the first plate, said second plate comprising a top side, a bottom side, and an outer edge around the perimeter of the plate, the plate comprising a fluid containment border around at least a portion of the outer edge, said second plate comprising one or more wells, each of said one or more wells comprising a well wall, a third plate disposed beneath the second plate, said third plate comprising a top side, a bottom side, an outer edge around the perimeter of the plate, a fluid containment border around at least a portion of the outer edge, wherein when said first plate, said second plate and said third plate are associated together in a resting position, at least one well of the second plate is aligned with at least one well of the first plate thereby providing a fluid communication there between, and said second plate abuts against the top side of the third plate to form at least one fluid sealed well the method comprising:
  providing a first plate vertically disposed above a second plate, wherein the first plate comprises one or more wells, said wells configured to receive a sample;
  providing a fluid delivery system coupled to the well plate system, said fluid delivery system comprising a pump and a fluid conduit to deliver a first fluid to one or more wells of the second plate, wherein once the one or more wells of the second plate are at least partially filled with the first fluid, any excess of the first fluid is removed from the second plate by at least one drain conduit;
  vertically lowering with a first motor the first plate onto the second plate, wherein the one or more wells of the first and second plates are vertically aligned, such that the first fluid from the one or more wells of the second plate passes through the one or more wells of the first plate and contacts the sample;
  vertically raising the first plate with the first motor, wherein the first fluid drains from the one or more wells of the first plate into the one or more wells of the second plate; and
  vertically raising the second plate with the first motor such that a seal between the second and the third plate is broken wherein the first fluid drains from the second plate onto the third plate and through at least one drainage opening in the third plate.

24. The method of claim 23, further comprising vertically lowering the second plate with the first motor onto the third plate creating a seal between the one or more wells of the second plate and the third plate, activating the fluid delivery system to initiate the pump to deliver a second fluid into the second plate via the conduit, wherein the second fluid is delivered to the one or more wells of the second plate.

25. The method of claim 23, further comprising horizontally moving the plate by the second motor to provide a mechanical agitation of the plate.

26. A well plate system, comprising:
  a well plate device;
    a first plate comprising a top surface, a bottom surface and an outer edge surface, said first plate having openings extending from the top surface to the bottom surface, wherein each of said openings are configured to receive a well comprising a wall and a bottom surface;
    a second plate comprising a top surface, a bottom surface and an outer edge surface around the perimeter of the plate, said second plate comprising a fluid containment border around said outer edge surface, said second plate having openings extending from the top surface to the bottom surface, said openings configured to receive a well, said well comprising a wall, wherein the openings of the first plate and the openings of the second plate are vertically aligned and at least one opening of the second plate is configured to receive a well of the first plate;
    a third plate comprising a top surface, a bottom surface, and an outer edge surface around the perimeter of the plate, said third plate having drainage openings extending from the top surface to the bottom surface, and a border surrounding at least a portion of the outer edge; and
  a first motor electrically connected to at least one of the first, second and third plates to provide movement of at least one of the plates relative to at least another of the plates, wherein the first motor is configured to move at least the first plate relative to the second plate.

* * * * *